United States Patent [19]

Schjeldahl et al.

[11] 4,456,000
[45] Jun. 26, 1984

[54] EXPANDABLE OCCLUSION APPARATUS

[75] Inventors: Gilmore T. Schjeldahl, Minnetonka, Minn.; B. Sharma, Springfield, Ill.

[73] Assignee: Angiomedics Corporation, Minneapolis, Minn.

[21] Appl. No.: 525,943

[22] Filed: Aug. 24, 1983

Related U.S. Application Data

[60] Division of Ser. No. 293,466, Aug. 17, 1981, Pat. No. 4,413,989, which is a continuation-in-part of Ser. No. 185,273, Sep. 8, 1980, abandoned, which is a continuation-in-part of Ser. No. 47,353, Jun. 11, 1979, abandoned.

[51] Int. Cl.³ .................... A61B 19/00; A61M 25/00
[52] U.S. Cl. ..................................... 128/1 D; 604/49
[58] Field of Search .................. 128/1 D; 604/47–49, 604/41, 52, 93, 96, 99, 104, 49

[56] References Cited

U.S. PATENT DOCUMENTS

| | | | |
|---|---|---|---|
| 3,707,151 | 12/1972 | Jackson | 604/96 X |
| 3,833,003 | 9/1974 | Taricco | 604/96 |
| 4,077,396 | 3/1978 | McCurdy | 128/1 D |
| 4,299,226 | 11/1981 | Banka | 604/53 |

Primary Examiner—Stephen C. Pellegrino
Attorney, Agent, or Firm—Orrin M. Haugen; Thomas J. Nikolai

[57] ABSTRACT

A catheter assembly or catheter attachment for use in treatment of coronary artery disease resulting from atheromatous lesions whereby stenotic lesions can be dilated without interruption to the blood supply distal to the stenotic lesion being treated, the catheter further allowing blood pressure distal to the site to be measured throughout the treatment procedure. In one form of the invention, the catheter assembly comprises first and second coaxial telescoping tubes, the outer tube having a pattern of perforations through its side wall proximate the distal end thereof and an inelastic expander member sealed to its outer surface at spaced apart locations so as to span the pattern of perforations. The patient's own blood may be perfused through the lumen of the outer tube between the outer surface of the inner tube and the inner surface of the outer tube and through the pattern of perforations to uniformly expand the inelastic expander member. The inner and outer tubes are tapered at their distal ends so as to facilitate insertion of the catheter assembly through a blood vessel and, by relative longitudinal displacement of the inner tube with respect to the outer tube, the pressure and rate of flow of blood from the open distal end of the catheter can be controlled from its proximal end. In an alternative arrangement, the inner tube is replaced with a cylindrical wire of a predetermined diameter less than the inner diameter of said outer tube. Further, the distal end portion of the outer tube may be made distensible so that it can be made to expand by applying a suitable pressure at the proximal end of the catheter, and the catheter may be provided with a highly flexible guidance pigtail for facilitating the insertions of the instrument into a blood vessel, without interfering with the expanding and perfusing functions of the instrument.

4 Claims, 11 Drawing Figures

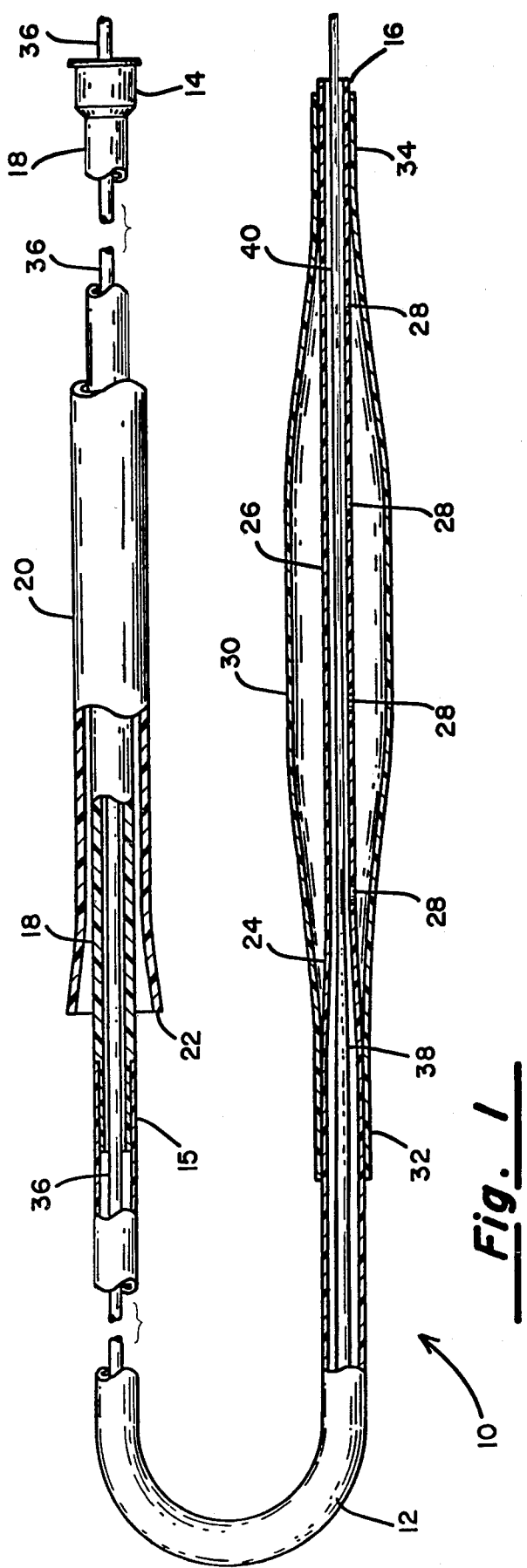
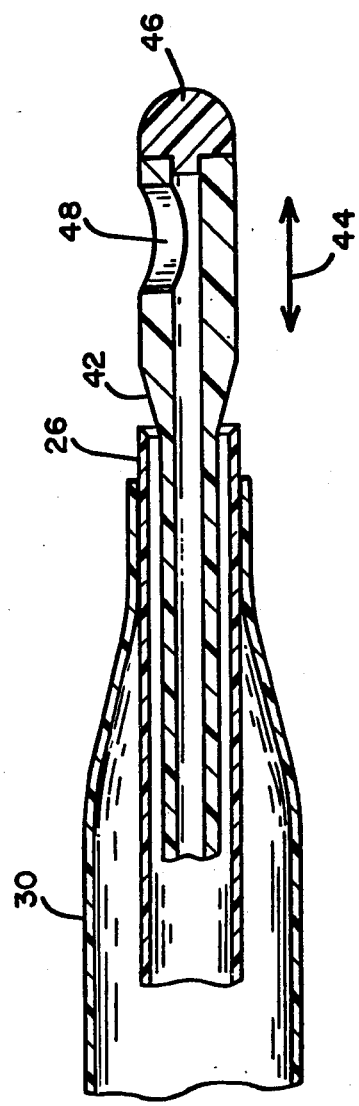
Fig. 1
Fig. 2

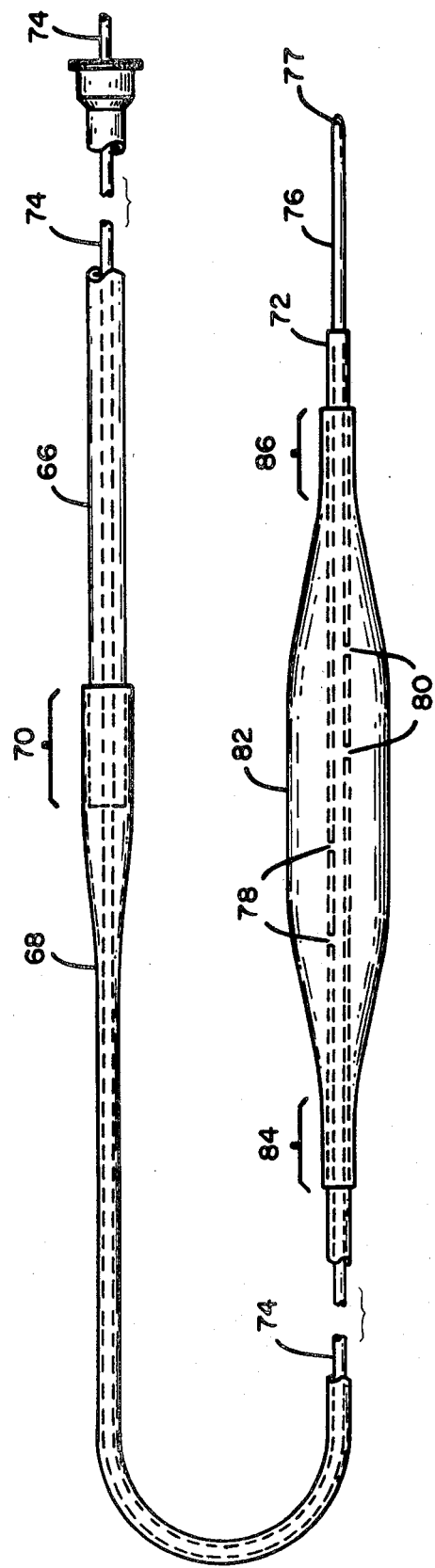
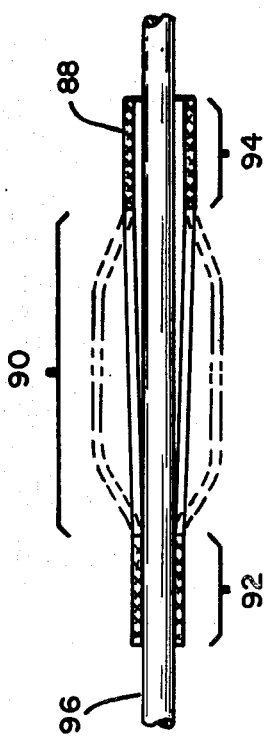
Fig. 6
Fig. 7

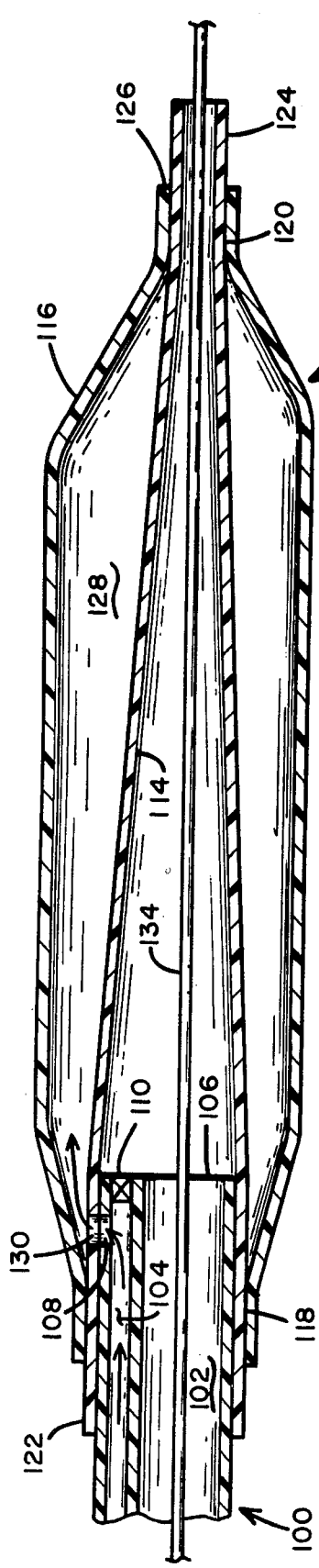
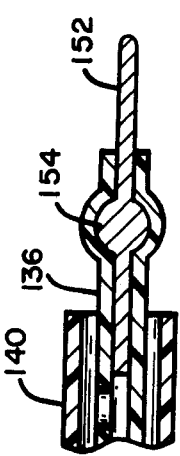
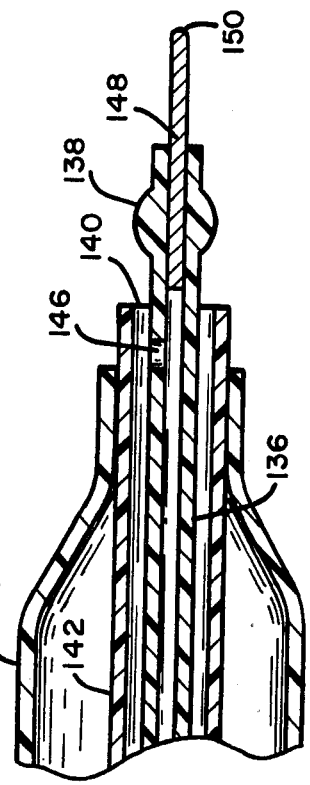
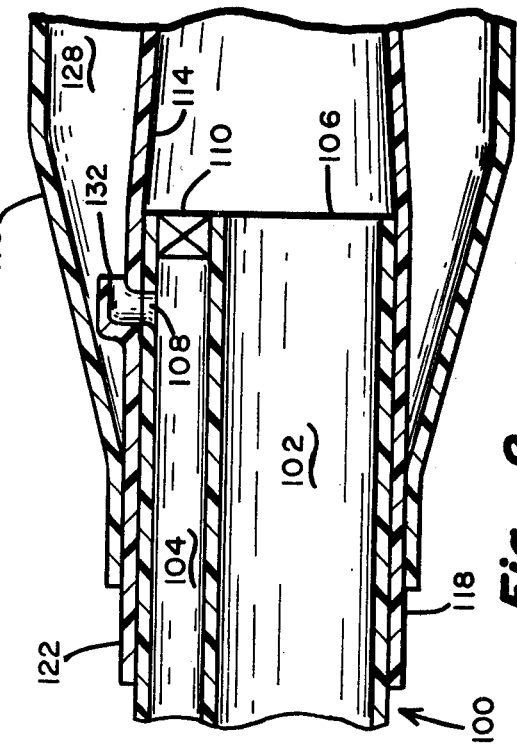

EXPANDABLE OCCLUSION APPARATUS

CROSS-REFERENCE TO RELATED APPLICATION

This is a division of application Ser. No. 293,466, filed Aug. 17, 1981 now U.S. Pat. No. 4,413,989, which is a continuation-in-part application of application Ser. No. 185,273, filed Sept. 8, 1980 and entitled "EXPANDABLE OCCLUSION APPARATUS" now abandoned, which is a continuation-in-part of application Ser. No. 47,353, filed June 11, 1979 and also entitled "EXPANDABLE OCCLUSION APPARATUS" now abandoned.

TECHNICAL FIELD

This invention relates to the field of surgery, in more particularly to instruments for facilitating the performance of surgical procedures involving the flow of blood in the larger blood vessels.

BACKGROUND OF THE INVENTION

I. Field of the Invention

The present invention is directed to the design of catheter structures for use in the treatment of coronary stenoses or other vascular obstructions, and more specifically to the design of a CTA/CP (coronary transluminal angioplasty/coronary perfusion) catheter assembly or attachment which facilitates the placement of an expander in a blood vessel at the site of an atheromatous lesion for inflation to apply a predetermined pressure on the lesion to dilate same while still permitting communication with the blood vessel at a site distal to the inflated expander member.

II. Discussion of the Prior Art

Obstructive coronary artery disease is generally recognized as a serious health problem in the United States and most of the western world. When drug treatment fails or inadequately controls angina pectoris, coronary artery bypass graft surgery is generally used.

In 1964, C. T. Dotter and M. P. Judkins introduced a transluminal coaxial catheter dilatation method for dilating atheromatous lesions in peripheral arteries. This technique required sequential dilation of stenotic lesions and employed progressively larger dilating catherters. The technique failed to gain wide acceptance, incidences of endothelial damage leading to frequent complications. Then, in 1971, Zeitler, Schoop and Zahnow reported the use of a "Fogarty Balloon Catheter" to perform transluminal arterioplasty. Subsequently, A. Gruntzig, M.D., employed the techniques reported earlier by Dotter, Zeitler and others, using a single double-lumen catheter with a distensible (balloon) segment at its tip which was positioned in the lumen at the stenotic segment of a peripheral artery. The elastic balloon segment was then inflated, resulting in compression of the atheromatous lesion in a manner perpendicular to the vessel wall, thus dilating the lumen. The balloon remained inflated about 10–15 seconds at 7 atmospheres internal pressure and then was deflated. It was found that there was a significant reduction in complications due to endothelial damage, such as that caused by earlier reported coaxial transluminal dilation techniques, and marked improvement in vessel patency through the use of the improved catheter. In a paper entitled "Coronary Percutaneous Translumenal Angioplasty: Preliminary Results" *Circulation* 57, 58 (Supp. II): II-56, 1978, Dr. Gruntzig presented data on 80 patients suffering from severe angina which data was obtained approximately six months following dilation of occluded coronary arteries using small diameter double-lumen CTA (coronary transluminal angioplasty) catheters. Of the 54 patients out of 80 on whom the dilation was successful, 90 percent indicated a significant pain improvement and patency of the dilated obstructions.

From evidence to date, coronary transluminal angioplasty (CTA) appears to offer a very promising therapeutic technique in symptomatic patients having coronary artery disease. See, for example, "Transluminal Coronary Artery Dilatation" by S. H. Stertzer et al, *Practical Cardiology* Vol. 5, No. 3, March, 1979. It is believed however, that problems still exist with balloon-tip catheters of the type employed to date for dilatation of atheromatous lesions in coronary arteries (see Editorial Report, Circ., Vol. 60, Page 969, 1979). Specifically, the amount of pressure which can be applied through the balloon-type expander is believed to be insufficient to dilate certain stenotic lesions. Then too, the use of the technique and catheter as presently employed by Gruntzig and others results in a total cessation of blood flow distal to the site of the treatment. In this regard, studies in living dogs with normal coronary arteries have shown that CTA may be associated with brief, self-limited ventricular tachycardia. During the inflation of the balloon, distal coronary pressure falls to zero. Because of the lack of blood flow and pressure distal to the treatment site, the period of dilation must be relatively short to prevent complications due to the lack of a blood supply. It is felt that this short period of dilatation may contribute to the reduction in the success rate of the coronary transluminal angioplasty (CTA) procedure.

SUMMARY OF THE INVENTION

The present invention is concerned with an improvement over prior art catheter structures useful in performing transluminal dilation and/or blockage of blood vessels. Catheters made in accordance with the teachings of the present invention permit significantly higher pressures to be applied to a given class of stenotic lesions without increase in the diameter of the relatively thin-wall balloon expander membrane and the pressures may be applied for longer periods of time in that the catheter of the present invention permits the perfusion of blood therethrough such that a controlled flow and pressure may be maintained distal to the treatment site.

These features and advantages are achieved in one embodiment through the novel design of a CTA/CP catheter assembly having a first, elongated, flexible outer tubular member, hereinafter referred to as the "high-torque tube", containing a generally coaxial, elongated, flexible inner tubular member disposed in its lumen. The inner diameter of the outer tube and the outer diameter of the inner tube are dimensioned to provide a predetermined clearance. An attachment to the distal end of the high-torque tube, referred to herein as the "expander mounting tube", has a pattern of perforations through its side wall proximate the distal end thereof. Surrounding the distal end and sealed to the expander mounting tube on either side of the pattern of perforations is an expander formed from a thin, flexible, inelastic, high tensile strength, biaxially oriented synthetic plastic material. Extending through the lumen of the high-torque tube and through the lumen of the expander mounting tube is a further tube, hereinafter referred to as the "pressure sensing tube". It, like the expander mounting tube attachment, is tapered from a larger diameter to a lesser diameter in approaching the distal end of the CTA/CP catheter assembly. Both are preferably made of a soft, flexible plastic material. In accordance with a second arrangement where it is deemed unnecessary to monitor the blood pressure distal to the expander, the pressure sensing tube may be replaced with a solid, generally cylindrical, flexible, guide wire of a predetermined diameter relative to the diameter of the lumen of the expander mounting tube. In adopting this latter approach, the need for a guide catheter may be obviated.

In use, the CTA/CP catheter assembly may be routed through the femoral artery, the left or right common iliac and the abdominal aorta and from there through the arch of the aorta and into the right or left coronary arteries. The expander portion of the catheter is juxtaposed with a stenotic lesion which may be present in the coronary artery and a supply of the patient's own blood or other suitable oxygen transporting fluid which may include medication is introduced, under pressure, at the proximal end of the CTA/CP catheter assembly and made to flow in the clearance space between the inner surface of the expander mounting tube and the outer surface of the pressure sensing tube or guide wire, as the case may be. Upon reaching the pattern of perforations proximate the distal end of the expander mounting tube, the blood flows through the perforations in the side wall so as to fill the flexible, inelastic expander causing it to expand, first to envelop the obstruction without applying a dilatation force to it, thereby establishing a reference or baseline for subsequent measurements, and then the fluid pressure may be increased, causing the expander to expand uniformly to a pre-calculated maximum diameter, thereby applying a pre-calculated and monitored pressure to the coronary stenoses. Then, by controlling the relative axial positioning of a tapered pressure sensing tube or the guide wire within the expander mounting tube, the physician can control the perfusion of blood out the distal end of the CTA/CP catheter assembly and beyond the now-expanded expander. If a non-tapered guide wire (or tube) is utilized, pressure can be maintained by proper design of the restriction in the region of the distal sleeve of the expander and proper control of the flow rate. By utilizing a manometer or other suitable pressure measuring device at the proximal end of the CTA/CP catheter assembly, (the device being connected to the pressure sensing tube), the pressure distal to the obstruction can be measured independently of the expander pressure throughout the treatment procedure and adjusted to fit the needs of the patient. However, when a solid, non-tapered wire is used, constant expander pressure can be maintained by proper design of the restriction in the region of the distal sleeve of the expander and by accurately monitoring fluid flow rate into the proximal end of the CTA/CP catheter assembly.

Due to the capabilities of simultaneous coronary dilation and perfusion, it is believed to be possible to perform coronary transluminal angioplasty procedures in critically ill patients including those suffering from unstable angina, enabling preservation of myocardium in actue myocardial infarction and in selected groups of patients with cardiogenic shock. Through the use of the CTA/CP catheter assembly of the present invention, if critically ill patients fail to respond to the dilatation treatment, it is contemplated that coronary perfusion can be enhanced beyond the obstruction while the patient is awaiting coronary artery bypass graft surgery.

By providing for the pumping of the patient's own blood through the blocked portion of the coronary artery while the occlusion is being pushed back into the wall of the artery, it is believed that the potential for causing a critical muscle cramp (angina), heart attack, and sudden death due to rhythm disturbance during the angioplasty procedure will be greatly reduced.

Furthermore, by the nature and the construction of the material, the non-elastic expander (balloon) disposed proximate the distal end of the expander mounting the attachment which will expand to a pre-formed diameter, furnishes a means whereby pressure exerted to the inner wall of the artery during the dilation procedure can be precisely measured. Obviously, therefore, the amount of force applied against the inner lining of the artery is both measurable and controllable. Medical personnel carrying out the transluminal angioplasty procedure will thus be able to carefully monitor the pressure within the non-elastic expander as a function of the rate of fluid flow at the proximal end of the CTA/CP catheter assembly and can maintain this pressure at a value calculated not to damage the wall of the vessel being treated. At the same time, one embodiment of the CTA/CP catheter assembly of the present invention allows the blood pressure in the blocked portion of the vessel being treated to be continuously monitored during the entire treatment procedure.

In addition to use as a catheter for performing the CTA/CP procedure mentioned, the catheter structures of this invention may also find use in maintaining critically ill cardiac patients experiencing congestive heart failure, angina, myocardial infarction or cardiogenic shock. In this regard, the CTA/CP catheter assembly may be routed through the vascular system, through the aorta and into a coronary artery. The expander can then be inflated by including the patient's own blood through the proximal end of the CTA/CP catheter assembly and permitting it to perfuse out the distal end at a desired rate, the expander (balloon) serving to block the coronary artery and to prevent backflow of the perfused blood back into the aorta. In this fashion coronary circulation is established to distribute blood, containing oxygen, nutrients, and other substances, to the cardiac muscle cells whereby recovery and repair may be enhanced.

The present invention also comprises means whereby the surgeon can adapt the conventional Simpson catheter, which is well known and is usually available in a number of sizes, to this use, when it is desired to use different fluids for expanding and perfusing. In this respect the invention comprises a tip member for affixation of the distal end of a Simpson catheter, and the combination of the catheter with the tip member. Further the invention comprises a structure in which a highly flexible pigtail tip is provided, for facilitating the insertion of the catheter or attachment into the blood vessel of interest, without interfering with the other functions of the catheter.

OBJECTS

Accordingly, it is a principal object of the present invention to provide new and improved catheter structures for use in coronary transluminal angioplasty treatment of coronary stenoses.

A further object of the invention is to provide CTA/CP catheter assemblies which may be used to selectively block a blood vessel and perfuse the patient's own blood or other suitable oxygen-bearing and possibly medicated fluid distally of the location so blocked, whereby conditions such as congestive heart failure, angina, myocardial infarction or cardiogenic shock may be treated.

Another object of the invention is to provide single lumen CTA/CP catheter assemblies which include an inelastic expander which when deflated may be routed through the arterial paths of the body to a site where angioplasty treatment is to occur and later expanded to a predetermined maximum diameter to apply a dilation force to the artery in the site of the stenotic lesion while at the said time permitting a controlled flow of blood or equivalent nutrient fluid, distal to the treatment site.

These and other objects and advantages of the present invention will become apparent to those of ordinary skill in the art from the following detailed description of the preferred embodiment when considered in conjunction with the accompanying drawings in which like numerals in the several views refer to corresponding parts.

BRIEF DESCRIPTION OF THE DRAWINGS

FIG. 1 is an enlarged, partially cross-sectioned, side elevation view of the embodiment of the invention;

FIG. 2 is a greatly enlarged view of the distal end of the CTA/CP catheter of FIG. 1;

FIG. 6 shows an alternative embodiment in which the pressure sensing tube of the embodiment in FIG. 1 is replaced with a solid wire;

FIG. 7 shows a still further embodiment of the invention;

FIG. 8 is a fragmentary view in axial section of another embodiment of the invention, greatly enlarged;

FIG. 9 is similar view of a modification of this embodiment;

FIG. 10 is fragmentary similar view of a further embodiment of the invention; and FIG. 11 is similar view of a modification of that embodiment

DESCRIPTION OF THE PREFERRED EMBODIMENTS

Figure 3:
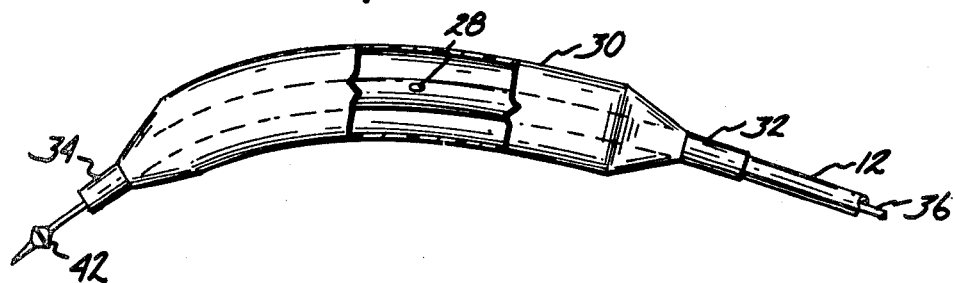
FIG. 3 is an enlarged view of the expander portion of an alternative embodiment.

Referring first to FIG. 1, there is shown a side elevation view, partially in cross-section, of one preferred form of a CTA/CP catheter assembly for facilitating transluminal angioplasty procedures in humans and other animals. The CTA/CP catheter assembly is indicated generally by numeral 10 and includes an elongated, flexible, plastic outer tubular member attachment referred to herein as the expander mounting tube 12 having a proximal end 15 and a distal end 16. The expander mounting tube 12 may have an outside diameter in the range of from 0.025 to 5.0 millimeters at its distal end 16, the dimension opening upon the particular size of the vessel to be treated. A correctly tapered expander mounting tube, for example, having an outer minimum diameter of 0.75 millimeters and an inside minimum diameter of 0.58 millimeters, has produced expander pressures and distal fluid flow which are altogether workable in treatment of coronary artery disease. The expander mounting tube 12 is preferably formed from a distensible synthetic plastic material such as silicon, polyurethane, polyethylene or polyvinylchloride.

Joined to the proximal end 15 to the expander mounting tube 12 is a segment of tubing hereinafter called a high-torque tube 18, which includes wire mesh reinforcing in the cylindrical walls thereof. The distal end 15 of the high-torque tube 18 is of substantially the same outer diameter as the inner diameter of the proximal end 14 of the expander mounting tube 12 and is fitted within the lumen of the proximal end 14 of the expander mounting tube 12 and either bonded or shrink fitted so that a torque applied to the proximal end of the high-torque tube will be transmitted to the expander mounting tube 12 in a manner to thereby facilitate its routing or passage through a desired blood vessel.

In FIG. 1 there is also shown a portion of a guide catheter 20 which is a commercially available device and which, in the carrying out of transluminal angioplasty procedures, may be inserted in the femoral artery and routed through the arterial system so that its distal end 22 engages the coronary ostium. Typically, the guide catheter 20 may be a 9 French catheter, this size being exemplary only as compatible with the size set forth above for the CTA/CP assembly 10.

The expander mounting tube 12 may be of generally constant diameter over substantially its entire length until a point is reached near its distal end where it may be found advantageous to taper this tube as at 24 to a terminal segment 26 of a reduced diameter. Tapering of the expander mounting tube 12 in the manner indicated creates a "choke" which maintains a given expander pressure at a given accurately controlled fluid flow rate through the lumen of the expander mounting tube 12 and further facilitates the entry and routing of the CTA/CP catheter tip through small diameter lesions.

Formed through the side wall of the expander mounting tube 12 in the constricted zone 26 is a pattern of apertures, as at 28.

Surrounding the distal end portion 26 of the expander mounting tube 12 is an expander 30 which, in FIG. 1, is shown in its extended condition. The expander 30 is preferably formed from a synthetic synthetic plastic material, such as biaxially oriented polypropylene, by an injection blow molding operation and, as such, is substantially inelastic in both the axial and radial directions and may, for example, have a finished wall thickness in the range of from 0.005 to 0.200 millimeters, 0.025 millimeters being typical. The expander 30 may be ultrasonically bonded or otherwise sealingly attached to the outer surface of the expander mounting tube 12 as at locations 32 and 34 so that the zone therebetween spans the apertures 28 and is free to expand and contract through the application of pneumatic or hydraulic forces to the proximal end 19 of the CTA/CP catheter assembly 10. Apertures 28 are of such diameter as to drain expander 30 adequately (for example in 2 seconds time) when a proper vacuum is applied at proximal end 19 of the CTA/CP10. It has been found that an expander of the above-dimensional characteristics can withstand internal inflation pressure in excess of 7 atmospheres without fear of rupture.

Again, because dimensional parameters depend upon the inner diameter of the vessel treated, the sizes and dimensions set forth herein are not absolute, but are included to provide the reader with an appreciation of the relative proportions involved. With this in mind, the expander 30 of FIG. 1 may have a fixed outer diameter, when expanded, in the range of from 1.0 to 30.0 millimeters and an overall length in the range of from 5 to 100 millimeters.

Extending through the lumen of the expander mounting tube 12 is a inner tube 36 which is also referred to herein as the "pressure sensing tube" for reasons which will become apparent when the overall operation of the device is set forth. The pressure sensing tube 36 may also be formed from the same materials as used in the construction of the expander mounting tube 12, namely, silicone rubber, polyurethane, polyethylene or polypropylene. The outside diameter of the pressure sensing tube 36 may, for example, be 0.57 millimeters, thereby providing a predetermined clearance space between the outside diameter of the pressure sensing tube 36 and the inside diameter of the expander mounting tube 12. However, the pressure sensing tube may have an outer diameter in the range of from 0.2 to 3.0 millimeters, provided the expander mounting tube 12 is properly sized.

Alternatively, where the pressure sensing feature is not required, the inner tube 36 may simply comprise a solid, generally cylindrical, flexible wire of a predetermined diameter in the range of from 0.2 to 3.0 mm, depending upon the size of the lumen of the expander mounting tube. A core wire of the type used in guiding angiographic catheters is altogether suitable, in that such wires are generally flexible and do not take on a set even when kinked sharply. The tip of the core wire, i.e., its distal end, may be preformed in any conventional shape to facilitate its entry into a selected coronary artery. More will be said later on herein when the embodiment of FIG. 6 is explained.

With continued reference to FIG. 1, it can be seen that the pressure sensing tube 36 is also tapered as at 38 to a segment 40 of a reduced diameter which is coextensive with the zone 26 of reduced diameter of the expander mounting tube 12. Further, and with reference to the greatly enlarged, cross-sectional, partial view of FIG. 2, it can be seen that the distal end portion of the pressure sensing tube 36 extending beyond the distal end 16 of the expander mounting tube 12 is tapered as at 42 at a predetermined angle so as to have a gradually increasing outside diameter as the distal end of the pressure sensing tube 36 is approached. The tapered portion 42 acts as a valve. That is, one may partially or totally occlude the distal end opening of the expander mounting tube 12 with the tapered segment 42 by axially displacing the pressure sensing tube 36 in the direction indicated by the double-headed arrow 44. Because the pressure sensing tube 36 comprises one continuous length, it is possible to achieve this axial displacement by manipulating the tube at the proximal end 19 of the CTA/CP assembly 10.

To avoid possible damage to the endothelial layer of the vessels during insertion of the catheter, it is desirable to provide a rounded tip 46 on the distal end of the pressure sensing tube 36 and a port 48 immediately rearward thereof which exposes the distal end of the pressure sensing tube 36 to the pressure existing in the vessel beyond the distal end of the tube. Of course, if a guide or core wire is used in place of the pressure sensing tube 36 as mentioned above, it too should have a smooth rounded distal tip to avoid damage to the blood vessels.

To properly route the catheter of the present invention through the patient's blood vessels, it is desirable that the catheter structure be radiopaque. This may be accomplished by providing a very thin layer of lead or other suitable material on either or both surfaces of the expander 30 during its manufacture. Alternatively, the inside surface of the expander 30 may be coated with a suitable dye commonly used in the conduct of angiographic examinations. Because of the desired thinness of the walls of the expander 30, difficulty has been experienced in incorporating radiopaque barium compounds in the plastic used to form the expander 30 in that that additive creates voids in the plastic and substantially decreases its wall strength. However, by employing the lead coating technique and/or the dye coating during or subsequent to the injection blow molding step used to form the expander 30, altogether satisfactory results have been achieved in rendering the surface of the expander member radiopaque.

Now that the details of the construction of one embodiment of the CTA/CP catheter assembly 10 of the present invention have been explained, consideration will next be given to the manner in which the device may be used in carrying out the transluminal angioplasty procedure.

OPERATION

While CTA/CP catheter structures made in accordance with the teachings of the present invention may find use in the conduct of other surgical procedures, in explaining the operation, the invention will be considered in an application relating to coronary transluminal angioplasty/coronary perfusion (CTA/CP).

Prior to the insertion of the CTA/CP catheter assembly 10 of FIG. 1 into the patient's body, a suitable supply of blood may be first drawn from the patient and washed so as to leave only red blood cells and a fluid carrier. This fluid may be oxygenated and heparinized for later use. Next, a guide catheter such as 20 in FIG. 1 may be inserted in the left or right femoral artery using the Seldinger technique, the guide catheter 20 being advanced to the appropriate coronary ostium. Next, the properly prepared CTA/CP catheter assembly 10 is routed through the guide catheter 20 and positioned in the stenosed region of the coronary artery, the segment 26 surrounded by the still deflated expander 30 being disposed at the treatment site. The placement of the expander 30 relative to the site is enhanced because of the ability to apply a high-torque force via the high-torque tube 18 to the proximal end of the attached expander mounting tube 12. By applying a radiopaque coating to the inside surface of the expander 30, it is possible to track the progress of the CTA/CP catheter assembly through the arterial blood vessels through the use of X-ray monitoring equipment.

The previously procured and prepared blood supply is then introduced by way of a suitable pump at the proximal end 19 of the CTA/CP catheter assembly 10 into the lumen of the expander mounting tube 12 so as to flow between the outer surface of the pressure sensing tube 36 (or core wire, as the case may be) and the inner surface of the expander mounting tube 12. The pressurized blood reaches the apertures 28 formed in the wall of the expander mounting tube 12 and exits therefrom so as to fill the expander 30 causing it to expand. With only a modest pressure in excess of blood pressure applied, the expander 30 initally conforms to the profile of the lesion and the force applied thereto is essentially zero. This provides an accurate baseline for further pressure measurements. Subsequently, the pump pressure is increased, at a precisely controlled rate, and the expander 30 is made to expand to its pre-formed maximum size. In doing so, an accurately measured dilating force is applied to the atheromatous lesion, compressing it into the arterial wall. Simultaneously, with the treatment process, through instrumentation attached to the proximal end 19 of the CTA/CP catheter assembly system 10, the rate of fluid flow may be continually monitored. The expander pressure is monitored as a function of the rate of fluid flow. Furthermore, the physician may also control the coronary perfusion rate by appropriate axial displacement of the pressure sensing tube 36 within the lumen of the expander mounting tube 12. In this regard, the tapered portion 42 on the distal end of the pressure sensing tube 36 can be made to control the flow of blood from the distal end 16 of the expander mounting tube 12. Where the distal end of the guide catheter 20 is made to enter the coronary ostium of the heart, it provides an opportunity to introduce blood flow into the coronary artery proximal to the stenosis site as well as distally thereto.

Because the blood/fluid transmitted through the catheter is maintained under hyperbaric conditions, the red blood cells may approach a super-oxygenated state, thus increasing the functional value of the red blood cells.

Another advantage afforded through the use of the CTA/CP catheter assembly 10 which permits perfusion of blood past the stenotic lesion being dilated, is that if a complication arises in the angioplasty procedure requiring surgical attention, the artery can be supplied with blood/fluid over a relatively long term to allow time for preparation and execution of necessary surgery or other medical procedures.

ALTERNATIVE DESIGN ARRANGEMENTS

In the embodiment of FIG. 1, the expander 30 is generally straight and therefore suitable for compressing atheromatous lesions which may be present in substantially straight portions of a blood vessel. However, such lesions may also be found in curved zones in various blood vessels and, for this reason, it is deemed advantageous to have a CTA/CP catheter assembly 10 structure with an expander 30 which is curved when expanded so as to conform generally to the shape of the vessel in which the lesion to be treated is found. FIG. 3 is a partial view of a catheter structure having this characteristic. Specifically, the expander mounting tube 12 has an expander 30 sealingly secured thereto as at zones 32 and 34, there being at least one aperture 28 formed through the side wall of the expander mounting tube 12 in the zone enclosed by the expander 30. As before, a pressure sensing tube 36 extends through the lumen of the expander mounting tube 12 and exits from the distal end 16 thereof, there being a tapered enlargement 42 thereon which can be moved into a fluid blocking relationship with the lumen of the expander mounting tube 12 by proper manipulation of the pressure sensing tube 36 at the proximal end thereof.

The expander 30 in the embodiment of FIG. 3 is designed such that the lower semicircular half of the portion affixed to expander mounting tube 12 is of shorter length than the portion affixed to the upper semicircular half of that expander tube when the expander 30 is in its deflated condition. As such, the distal end portion 34 of the expander mounting tube 12 will be generally straight as the catheter is being manipulated through the blood vessel. However, when it is juxtaposed with respect to a lesion in a curved portion of a blood vessel, the patient's own blood may be introduced by way of a pump into the proximal end of the expander mounting tube 12 so that it flows through the lumen thereof outside of the outer walls of the pressure sensing tube 36 and exits by way of the aperture 28 into the chamber defined by the expander 30. As the pressure within the expander 30 increases, it will assume its precalculated maximum size and in doing so will impart a bending force on the expander tube 12 due to the unequal length dimensions of the upper and lower semicircular halves of the expander 30. Thus, the operative portion of the angioplasty catheter will assume a curved profile as indicated in FIG. 3.

Figure 4:
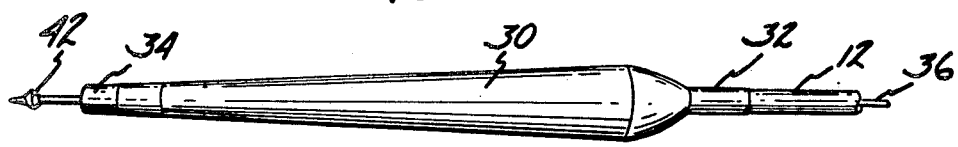
FIG. 4 is an enlarged view of the expander portion of a further alternative embodiment.

FIG. 4 illustrates a still further alternative configuration for the expander 30. In the embodiment of FIG. 4, when the expander 30 is infused with blood, it assumes a generally tapered profile, having a lesser diameter at or near the distal end that it does at its proximal end. As such, as the catheter is routed through the blood vessel, it presents a smaller, more pointed end to the stenotic lesions and by sequentially advancing, inflating, deflating, and further advancing, it is possible to work the expander 30 through the zone occupied by the lesion with lower risk of damage to the endotherial layer and with a diminished propensity toward dislodgment of pieces of the lesion which could possibly float to a constricted zone and create a total occlusion at that location. As with the embodiment of FIG. 1, in the arrangment of FIGS. 3 and 4, the expander 30 is formed from a biaxially oriented thin plastic material capable of withstanding relatively high internal pressures without rupture and without exceeding the elastic limit for the material itself. Hence, the expander member fills to a precalculated maximum size in an inelastic fashion. At the same time, blood may perfuse out the distal end of the expander mounting tube 12, the rate of blood flow being determined by the positioning of a pressure sensing tube 36 or a core wire 76 and especially its tapered enlargement 42 with respect to the distal end of the expander mounting tube 12.

Figure 5:
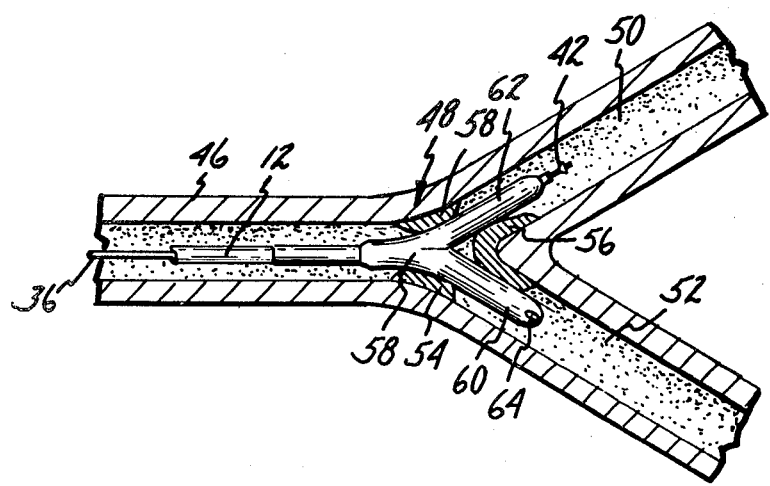
FIG. 5 is an enlarged view of a portion of the coronary artery illustrating the disposition of a still further alternative embodiment of the transluminal angioplasty catheter.

FIG. 5 illustrates a still further embodiment of the invention particularly suited for conducting coronary transluminal angioplasty procedures in a zone proximate a branch or node in a coronary artery or other similar location. Specifically, numeral 50 refers to, for example, the left coronary artery which artery divides at a branch point indicated generally by numeral 51 into the circumflex branch 52 and the anterior descending branch 53 of the left coronary artery. Pathologists have found that there is a tendency for focal accumulation of certain fatty proteins in the form of plaques at the branch point which may build to the point where the heart muscle or myocardium may have its normal blood supply greatly reduced. In FIG. 5, these fatty deposits proximate the branch point are identified by numerals 54, 56 and 58.

If a CTA/CP catheter assembly 10 of the type depicted in FIGS. 1, 3 or 4 is employed during the angioplasty procedure, only one such branch can be treated at a time. As such, there is a possibility that the application of a dilatation force between, say, the deposits 54 and 56 might result in a simultaneous occlusion of the vessel branch 52 and hence, a starvation of points distal of the deposits 56 and 58. To overcome this problem, the expander 30 of the embodiment of FIG. 5 is generally bifurcated, when in its expanded condition, to diverging branches 60 and 62. More specifically, as with the other embodiments, the catheter comprises an outer expander mounting tube 12 having a pressure sensing tube 36 passing therethrough and terminating in a distal end 42. The expander 30 is sealingly secured to the outer surface of the expander mounting tube 12 and a pattern of apertures is formed in the side walls of the expander mounting tube 12. As the catheter is being routed through the patient's arteries, the expander 30 is deflated and the branch 60 thereof is wrapped about the branch 62 in a way that reduces the overall cross-sectional size of the collapsed expander. Once the expander 30 is positioned proximate the branch point 51 of the coronary artery 50, blood is introduced into the lumen of the expander mounting tube 12 and it flows through the apertures formed therein so as to fill and expand the expander 30, causing the branch 60 to pop outwardly from the branch 62. As the blood supply into the composite expander 30 is increased, both branches 60 and 62 simultaneously expand and dilation forces are simultaneously applied between the deposits 56 and 58 and between the deposits 54 and 56. Blood is permitted to perfuse out the distal end 43 of the expander mounting tube 12 passing through the branch 62 in a controlled fashion determined by the axial positioning of the end portion 42 of the pressure sensing tube 36. The end of the expander branch 60 is provided with an orifice 64 of a predetermined size which permits a controlled flow of blood distal to the branch 60, i.e., into the vessel branch 53.

Because of the bifurcated shape of the expander 30 on the catheter, the lesions existing in both branches 52 and 53 are simultaneously treated. Also, blood flows distally of the treatment sites in both of the artial branches 52 and 53. The simultaneous application of the dilatation forces prevents collapse of one of the branches which would otherwise possibly result if only a single branch were treated at a given time.

The embodiment of FIG. 6 illustrates an arrangement wherein the pressure sensing tube is replaced with a guide wire of a predetermined diameter relative to the I.D. of the expander mounting tube whereby blood or other fluid may be perfused through the clearance between the outside diameter of the guide wire and the I.D. of the expander mounting tube. As is indicated, a conventional high-torque tube 66 is provided and it is terminated with an expander mounting tube 68 which is bonded to or otherwise secured to the high-torque tube 66 in a junction zone as at 70. The high-torque tube 66 may typically be a 5-French O.D. wire reinforced catheter and may have an inside diameter (I.D.) of 0.034 inches. The expander mounting tube 68 is tapered such that in the zone 70 it may have a O.D. of 0.076 inches and at its distal tip 72 may typically have a O.D. of 0.030 inches. The dimensions set out herein should be considered strictly as illustrative and not as limitive in that variations may be made to suit particular needs.

The expander mounting tube 68 may be formed from a variety of materials including polyurethane, polyvinylchloride or other suitable material which can be made distensible. The inside diameter of the expander mounting tube 68 may also vary in size from, say, 0.068 inches in the junction zone 70 where it mates with the high-torque tube 66 to about 0.024 inches at its distal tip 72. Disposed within the lumen of the high-torque tube 66 and the expander mounting tube 68 is a core guide wire 74 which is preferably of a constant diameter but which may, if desired, also be tapered along its length to accommodate predetermined flow characteristics for reasons yet to be described. With the typical dimensions thus far set out, the guide wire 74 may have a O.D. of 0.018 inches along its length. Such guide wires are commonly used in catheter arrangements designed for angiographic applications and are preferably of a type which can be bent sharply without taking on a permanent set. It is also feasible that the distal end 76 of the guide wire be shaped in the Judkins configuration, the Amplatz configuration or other suitable shape for facilitating the entry of the catheter into the various blood vessels. A rounded end 77 on the distal tip 76 of the guide wire is provided to minimize the likelihood of damage to the vascular system during manipulation thereof.

As in the embodiment of FIG. 1, the expander mounting tube 68 is provided with one or more holes as at 78, 80 extending through the side walls thereof at a location proximal of the distal end 72. Disposed on the expander mounting tube 68 is an expander 82 which, in FIG. 6, is shown in its extended condition. As in the embodiment of FIG. 1, the expander 82 is preferably formed from a suitable synthetic plastic material such as biaxially oriented polypropylene or biaxially oriented polyethylene terephthlate by an injection blow molding operation and, as such, is substantially inelastic in both the axial and radial direction. The wall thickness of the expander 82 may range between 0.0005 mm and 0.200 mm and depends upon the polymer used in its formation as well as on the method used in fabrication. The expander 82 terminates in a proximal sleeve zone 84 and a distal sleeve zone 86 which zones are on opposite sides of the ports or apertures 78–80. The expander member 82 may be held in place on the expander mounting tube 68 by a suitable adhesive layer in the sleeve zones 84 and 86.

An important feature of the embodiment of FIG. 6 is that the expander mounting tube 68 is fabricated so as to be distensible along at least a predetermined portion of its length from the distal tip end 72 proximally toward the connection zone 70. The sleeve zone 86 is, however, designed to be generally non-distensible, thus assuring a given expander volume pressure for a given rate of flow at the proximal end of the high-torque tube 66.

The catheter of the embodiment of FIG. 6 may be used in much the same fashion as the other arrangements for performing the CTA/CP procedure. That is, the CTA/CP catheter assembly is guided through the patient's vascular system until the non-expanded expander member 82 is disposed adjacent to a stenotic lesion to be treated. The patient's own blood or a suitable oxygen bearing and/or medicated fluid is introduced through the proximal end of the high-torque tube 66 and made to perfuse through the space between the outside diameter of the guide wire 74 and the inside diameter of the high-torque tube 66. The blood or other fluid also passes through the space between the guide wire 74 and the I.D. of the expander mounting tube 68 and when it reaches the ports or apertures 78–80, flows outwardly of the expander mounting tube 66 to inflate the expander 82 to its maximum size as illustrated in FIG. 6. By controlling the rate of flow applied to the proximal end of CTA/CP catheter assembly 10, the amount of force exerted on the stenotic lesion can be precisely controlled. In that the distal end portion of the expander mounting tube 68 attachment is designed to be distensible, the amount of blood or other fluid flowing out the distal end 72 of the expander mounting tube 68 is likewise a function of the rate of flow applied at the proximal end of the high-torque tube 66, the viscosity of the fluid, and the spacing between the central core wire 74 and the I.D. of the expander mounting tube 68 in region 86. Thus, by introducing a greater flow rate into the proximal end of the high-torque tube 66, a higher pressure can be achieved in the expander 82 volume accompanied by an increased outflow of fluid at the distal end 72. In that the sleeve zone 86 is designed to have much less distensibility than that of the expander mounting tube, it acts as a restriction against the outward expansion of the expander mounting tube, the sleeve zone 86 providing the necessary restriction such that a back pressure sufficient to fully inflate the expander 82 can be achieved while simultaneously permitting a controlled outflow of fluid at the distal end 72 of the expander mounting tube.

Because of the design of the expander mounting tube 68 attachment and its associated expander member 82, it may be fabricated as a separate piece and subsequently bonded to a standard, commercially available high-torque tube 66 in a bonding operation. It is further contemplated that expander mounting tubes and associated expanders of differing sizes may be provided in kit form to the physician so that during the CTA/CP procedure, he may select the particular size to accomplish a desired function and secured it to the high-torque tube.

The ports 78-80 formed through the side walls of the expander mounting tube are of a size and/or number adequate to provide complete drainage of the expander 82 volume within a predetermined time, say, two seconds, when proper suction is applied at the proximal end 14 of the CTA/CP catheter assembly. By successively positioning, expanding, deflating, and repositioning, the catheter of the present invention may be advanced through a blood vessel containing plural lesions in carrying out the transluminal dilatation technique.

Rather than employing a separate expander member 82 which is arranged to be slipped over the expander mounting tube 68 and bonded thereto in the sleeve zones 84 and 86, it is also contemplated that a catheter tip attachment suitable for use in carrying out the angioplasty technique may be fabricated by using selective irradiation of a length of plastic tubing whereby a zone may be masked during the irradiation process, shielding the plastic in that zone from the effects of the radiation. In this fashion, the shielded zone may be of a substantially lower hoop strength than the remainder of the tubing which had been subjected to selective orientation because of the irradiation step.

Referring to FIG. 7, there is shown a partial, greatly enlarged, sectional view of a unitary balloon tip attachment prepared using a selective irradiation process. In this arrangement, the tube attachment 88 is formed from a suitable plastic such as polyurethane, polyvinylchloride or the like. It is formed to a predetermined length and diameter (inside and outside) and subsequently masked in the zone identified by the bracket 90. Once so masked, the tube is subjected to a suitable source of radiation whereby the unmasked zones 92 and 94 receive the radiation and the molecules of plastic therein are cross-linked in a well-known manner to render the material in that zone relatively non-distensible as compared to the material residing in the masked zone 90. Again, a guide wire as at 96 is employed not only to facilitate the routing of the CTA/CP catheter assembly through the vascular system and into a particular coronary artery or branch thereof but also to serve as a flow control means.

Thus, when fluid, under pressure, is perfused between the guide wire 96 and the inside wall of the tube attachment 88, the shielded portion 90 of the tube 88 expands as indicated in FIG. 7 by the dotted lines in much the same fashion as a fusiform aneurysm. The expansible portion of the single lumen tube attachment 88 can then be juxtaposed in a zone of a stenotic lesion and when the rate of flow is increased at the proximal end of the high-torque tube 66, the pressure increases in the expander zone 90 because of the flow restriction in zone 92 distal to that point and the tube zone 90 expands and a force is applied to the lesion tending to drive it into the vessel wall.

In FIG. 8 there is shown a portion of a Simpson catheter 100 having a major lumen 102 and an independent minor lumen 104, terminating at the distal end 106 of the catheter. A lateral port 108 is provided near the distal end of lumen 104, which is closed by a plug 110 at a site distal to port 108.

A tip member 112 according to the invention comprises distensible a mounting tube 114 and an expander 116 secured together coaxially at proximal and distal joints 118 and 120. Tube 114 is of such diameter at its proximal end 122 as to receive and be affixed to end 106 of catheter 100, and tapers to a somewhat smaller diameter at its distal end 124, which projects slightly beyond the distal end 126 of expander 116.

The expander is of flexible but inelastic material, and is of a predetermined diameter larger than tube 114, to define a space 128 surrounding member 114. A port 130 is formed in the wall of tube 114 in alignment with port 108 of the catheter to afford communication between minor lumen 104 and space 128 just defined. When fluid under pressure is introduced into space 128, expander 116 assumes the configuration shown: any additional fluid forced into the space does not enlarge the expander, but distends tube 114 inwardly.

When fluid is withdrawn from expander 116, the latter collapes into irregularly pleated contact with tube 114. In the modification of the invention shown in FIG. 9 a port 132 is given such a configuration that collapse of expander 116 against it cannot seal the port and so interfere with complete removal of fluid from space 128.

For some applications it may desirable to provide a flexible core of tubing or wire 134 passing down catheter lumen 102 and out through the small end of tube 114. The end of core 134 is preferably configured as a guide for directing the catheter during insertion, or as a valve to regulate the flow fluid out of tube end 126, or both, as is known in such devices.

OPERATION

To use the invention a mounting tube and a Simpson catheter of sizes appropriate to the surgical procedure being comtemplated are selected. Port 108 is formed in catheter lumen 102 at the proper location, and the distal end of the lumen is sealed by a plug 110. The distal end of the catheter so prepared is inserted into the proximal end of the tube-member so that ports 108 and 130 or 132 are aligned, and affixed by adhesive or suitable means. If desired a core 134 is passed through the catheter and tube.

The catheter properly sterilized is inserted into the blood vessel of interest by standard percutaneous procedures, its location being monitored radiographically. When proper positioning has been accomplished, admission of a fluid such a saline solution through lumen 104 and ports 108 and 130 or 132 fills space 128, and expander 116 assumes its predetermined diameter, occluding the vessel in question. At the same time a flow of patients own blood or some other oxygen-bearing fluid may be inititated through lumen 102, the flow being limited, as called for by the operative procedure, by selection or adjustment of core 134.

After the surgical procedure is terminated, the fluid in space 128 is withdrawn by aspiration through ports 108 and 130 or 132, so that expander 116 collapses and the instrument may be withdrawn from the vessel to complete the procedure.

FIG. 10 shows a modification of the distal end of an instrument according to the invention. Here the end of a core in the form of a tube 136 is formed with a terminal nodule 138 of such size as to seal the distal opening 140 of the mounting tube 142 for an expander 144. Proximal of node of 138 a port 146 is formed in the wall of tube 136. To facilitate the insertion of the instrument into a blood vessel without interferring with the expanding or perfusing functions, a pigtail 148 of very flexible wire having a properly rounded end 150 is secured in and closes the end of tube 136.

FIG. 11 shows that if desired the distal end of tube 136 may be unmodified, and a pigtail 152 may be used having an integral node or bolus 154 which holds the pigtail in the tube and at the same time distends the latter to enable performance of the valving at the end of tube 140.

Thus it can be seen that there is provided by this invention apparatus whereby atherosclerotic deposits, such as may be found in coronary arteries, may be successfully dilated through the use of a coronary transluminal angioplasty/coronary perfusion (CTA/CP) catheter assembly without restricting the blood supply distally of the treatment site during the treatment steps. The invention has been described herein in considerable detail, in order to comply with the Patent Statutes and to provide those skilled in the art with information needed to apply the novel principles, and to construct and use such specialized components as are required.

However, it is to be understood that the invention can be carried out by specifically different equipment and devices, and that various modifications, both as to equipment details and operating procedures can be effected without departing from the scope of the invention itself.

What is claimed is:

1. A method of treating stenotic lesions in blood vessels comprising:
   (a) collecting a supply of the patient's blood;
   (b) providing a catheter having an elongated outer expander mounting tube, an inner pressure sensing tube disposed in the lumen of said outer expander tube, a flexible inelastic tubular expander member sealingly affixed at the opposed ends thereof to the outer surface of said expander mounting tube proximate the distal end of said catheter, there being a pattern of apertures formed through the side walls of said expander tube in the zone between said opposed ends of said flexible, inelastic expander member;
   (c) introducing said catheter into a blood vessel and positioning said expander member in alignment with the stenotic lesions to be treated;
   (d) pumping the patient's own blood from said supply, at a first predetermined pressure through the lumen of said expander mounting tube and through said apertures to inflate said expander member; and
   (e) subsequently increasing the pressure at which said blood supply is being pumped to dilate said lesion while simultaneously controlling the rate of flow of blood out from the distal end of said catheter.

2. The method as in claim 1 and further including the step of continuously monitoring the pressure at the distal end of said catheter at the proximal end of said pressure sensing tube.

3. The method as in claim 1 and further including the step of monitoring the fluid pressure within said expander member as said lesion is being dilated.

4. The method as in claim 1 and further including the step of treating said supply of blood prior to said pumping step.

* * * * *